United States Patent [19]

French et al.

[11] 4,011,925
[45] Mar. 15, 1977

[54] STETHOSCOPE

[75] Inventors: Alan French, Warwick; George Winthrop Torrey, West Barrington, both of R.I.

[73] Assignee: Avid Corporation, East Providence, R.I.

[22] Filed: Jan. 23, 1976

[21] Appl. No.: 651,640

[52] U.S. Cl. .............................. 181/131; 181/135; 181/137

[51] Int. Cl.² .......................................... A61B 7/02

[58] Field of Search ................. 181/131, 135, 137; 179/1 ST, 182 A, 182 R

[56] References Cited

UNITED STATES PATENTS

| | | | |
|---|---|---|---|
| 3,623,571 | 11/1971 | French | 181/135 |
| 3,730,290 | 5/1973 | Scanlon | 181/135 |
| 3,772,478 | 11/1973 | McCabe et al. | 179/1 ST |
| 3,776,362 | 12/1973 | Rice | 181/135 |
| 3,899,044 | 8/1975 | Stumpf et al. | 181/135 |

Primary Examiner—Stephen J. Tomsky
Attorney, Agent, or Firm—William Frederick Werner

[57] ABSTRACT

The present invention relates to stethoscopes of the type commonly employed by air line passengers for use with entertaining sound apparatus and is concerned primarily with a stethoscope which may be adjusted for comfort when applied to and suspended from the ear canals of an air line passenger.

5 Claims, 10 Drawing Figures

STETHOSCOPE

STATEMENT OF INVENTION

This invention relates to stethoscopes and more particularly to a unitary structure incorporating a living hinge provided with a friction adjustment, whereby opposite arms are held in selected relative position.

BACKGROUND OF THE INVENTION

Many commercial aircraft are today provided with sound systems for furnishing entertainment such as sound associated with a motion picture or stereo music, while the aircraft is in flight. Such systems may be provided with a plurality of channels for providing different modes of entertainment to different passengers while being non-disturbing to other passengers. In such systems the sound is piped from a fixed transducer through tubings to passenger's ears to enable, firstly, a substantial blockage of extraneous noise and, secondly, eliminating disturbance to other passengers. Moreover, accurate reproduction of the sound is desirable as well as the ability of the headset to conform to the physical characteristics of the head and ear span of any person who might be a passenger. The stethoscope must be light in weight, comfortable to the wearer while suspended from the ear canals and remain in position during normal head movement of the passenger. Further, inasmuch as the ear pieces of the stethoscope must be inserted in the passenger's ear canals, hygienic considerations require that the stethoscope, and particularly the ear pieces thereof, be either sterilizable or disposable and, where disposability is not required, it is desirable that the entire stethoscope be relatively inexpensive so as to reduce losses due to pilferage, misuse, breakage, and the like.

The present invention is considered to be an improvement over U.S. Pat. Nos. 3,623,571; 3,730,290; 3,776,362.

OBJECTS OF THE INVENTION

With foregoing conditions in mind, the invention has the following objectives in view:

1. To provide a stethoscope of such construction that the weight of the stethoscope, utilizing materials of the lightest weight, will weigh an absolute minimum so that, when suspended from the ear canal of a passenger for hours, it will cause no discomfort.

2. To provide a stethoscope of such construction that manufacturing costs make possible that economic fact that the stethoscope may be discarded after use by one passenger.

3. To provide a stethoscope of such construction that the frequency response in stereophonic sound is maintained as the sound waves pass through the stethoscope.

4. To provide a stethoscope of such construction that microscopic adjustment may be manually provided in ear span distance.

5. To provide a stethoscope molded in one piece and/or as a unitary structure.

Other objects of the present invention will be pointed out in part and become apparent in part in the following specification and claims.

BRIEF DESCRIPTION OF THE DRAWINGS

Referring to the drawings in which similar characters of reference indicate corresponding parts in all the figures.

In proceeding with this invention, reference is made to the drawings wherein is shown a stethoscope fabricated as a unitary structure. That is, a stethoscope molded as one piece including a living hinge and two friction joints, one for each arm.

Figure 1:
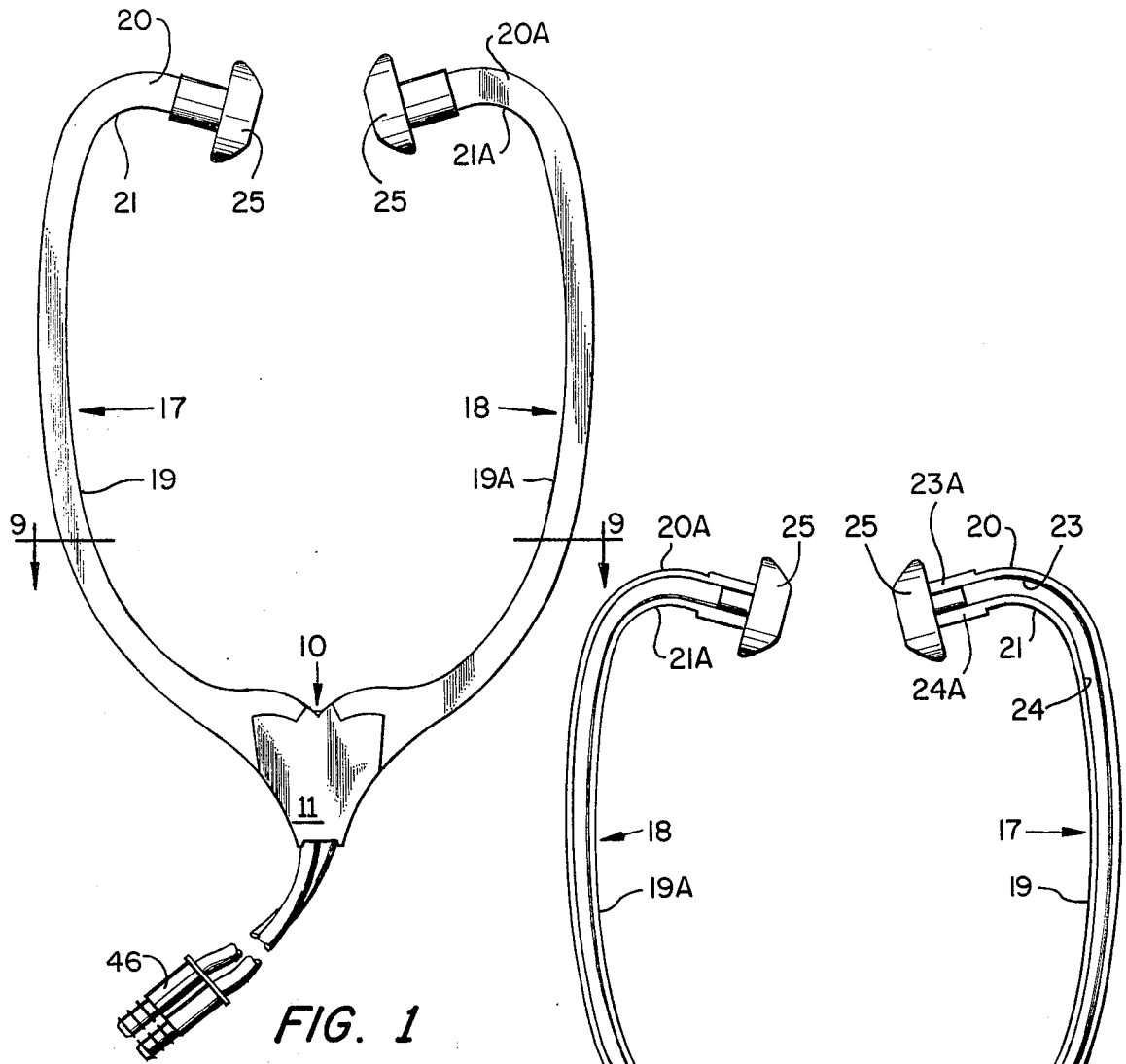
FIG. 1 is a front elevational view embodying the present invention.

The stethoscope, generally indicated by reference numeral 10, comprises a body 11 in the form of a flat plate having a raised elongated collar 12 provided with arcuate shaped, oppositely located, left wing 13 and right wing 14, as viewed from FIG. 1. A left arm stop 15 and a right arm stop 16 are provided on body 11.

Figure 2:
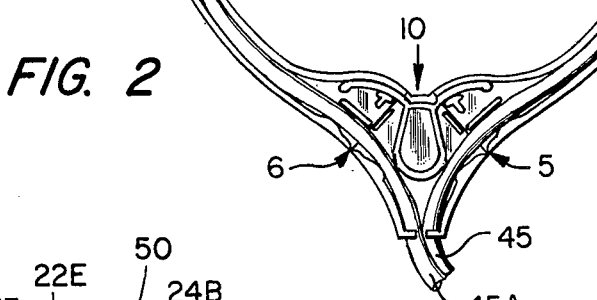
FIG. 2 is a rear elevational view of FIG. 1.
Figure 3:
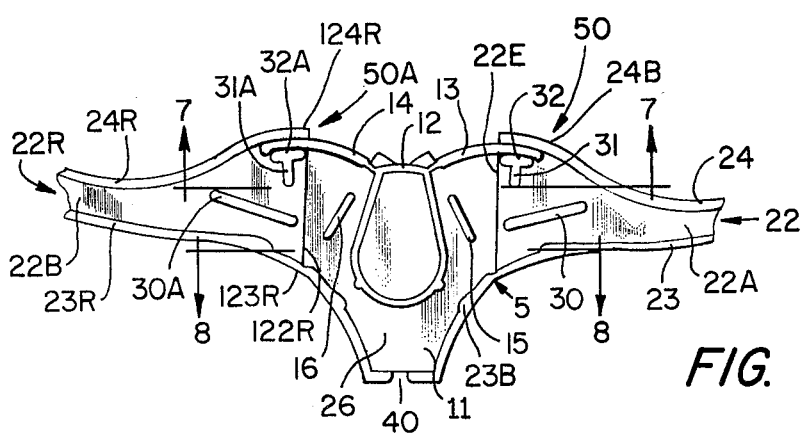
FIG. 3 is an enlarged sectional view of the living hinge showing the arms in maximum spread apart position.

Two arms are provided, generally designated as left arm 17 and right arm 18. Left arm 17 comprises a long section 19 and a short section 20 integrally joined to long section 19 by a bend or smooth curve 21. With reference to FIGS. 2 and 3, left arm 17 is provided with a channel 22 consisting of two walls 23, 24 and a base 22A. Channel 22 tends to make arm 17 rigid. The ends of walls 23, 24 at 23A, 24A (See FIG. 2) are thickened or reinforced. An ear tip 25 is inserted into channel 22 between walls 23A, 24A and projects therefrom. Ear piece 25 may be constructed in accordance with U.S. Pat. No. 3,539,031.

The opposite ends of walls 23, 24 are provided, respectively, with a left wall extension 23B integrally attached to body 11, so as to form one side of a chamber 26, and an arcuate section 24B having a cooperating contour with left wing 13. The base 22A of channel 22 terminates as base end 22E. A tube guide 30 is provided on base 22A. A friction pad 31 provided with an arcuate surface 32 is adapted to accommodate left wing 13 and is integral with base 22A. Left wing 13 frictionally slides between arcuate section 24B and arcuate surface 32 in a manner known as a friction joint and herein termed a left friction joint 50.

In like manner, right arm 18 comprises a long section 19A and a short section 20A. Right arm 18 is provided with a channel 22R consisting of two walls 23R, 24R and a base 22B. Channel 22R tends to make right arm 18 rigid. The ends of walls 23R, 24R are reinforced as previously described for left arm 17 and for the purpose stated.

The opposite ends of walls 23R, 24R are provided, respectively, with a right wall extension 123R integrally attached to body 11, so as to form one side of a chamber 26, and an arcuate section 124R having a cooperating contour with right wing 14. A slot 40 is provided between the ends of extensions 23B and 123R. The base 22B of channel 22R terminates as base end 122R. A tube guide 30A is provided on base 22B. A friction pad 31A provided with an arcuate surface 32A is adapted to accommodate right wing 14 and is integral with base 22B. Right wing 14 frictionally slides between arcuate section 124R and arcuate surface 32A and a right friction joint, generally indicated at 50A.

Figure 6:
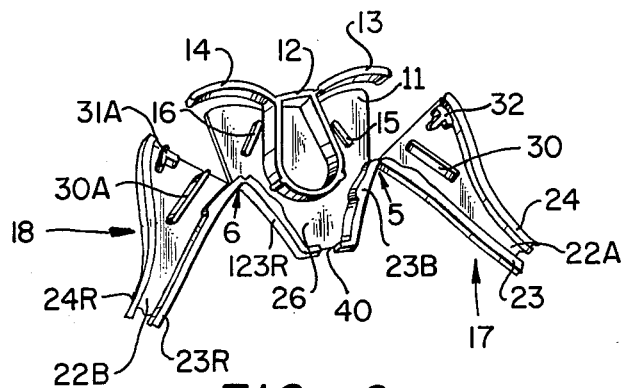
FIG. 6 is a fragmentary perspective view showing the construction of the living hinge.
Figure 7:
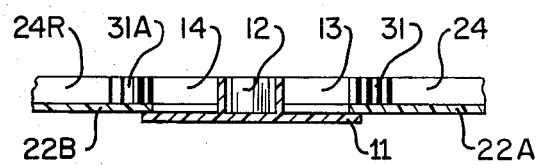
FIG. 7 is a fragmentary horizontal cross sectional view taken on line 7—7 of FIG. 3.
Figure 8:
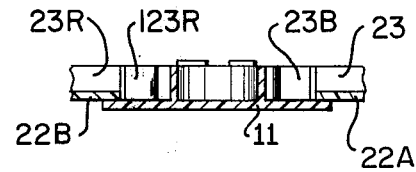
FIG. 8 is a fragmentary horizontal cross sectional view taken on line 8—8 of FIG. 3.
Figure 9:
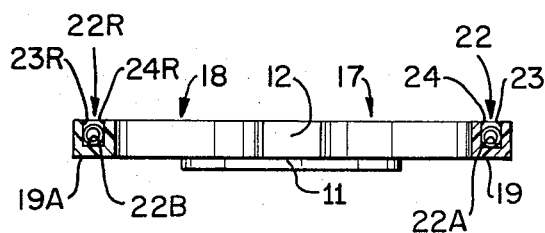
FIG. 9 is a horizontal cross sectional view taken on line 9—9 of FIG. 1.
Figure 10:
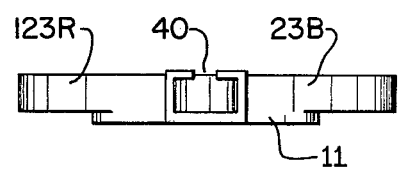
FIG. 10 is a bottom plan view of FIG. 1.

It will be observed with reference to FIG. 6 that extensions 23B and 123R, integrally connect, respectively, left arm 17 and right arm 18 to body 11.

It will be observed with respect to FIGS. 3, 4, 5 and 6 that at the intersection of wall 23 and left wall extension 23B, a flexible joint is formed connecting left arm 17 to body 11. This is left arm hinge, generally designated with reference numeral 5. Similarly, at the intersection of wall 23R and right wall extension 123R, a flexible joint is formed connecting right arm 18 to body 11. This is right arm hinge, generally designated with reference numeral 6.

Left arm pivots toward and away from body 11 around hinge 5 to permit left wing 13 to slidably and frictionally engage both arcuate section 24B and arcuate surface 32, functioning as left friction joint 50.

Similarly, right arm pivots toward and away from body 11 around hinge 6 to permit right wing 14 to slidably and frictionally engage both arcuate section 124R and arcuate surface 32A, functioning as right friction joint 50A.

The combination of the friction joint 50 and hinge 5 is termed a "living hinge" in the art.

Base end 22E abuts left arm stop 15 whereby pivotal movement of left arm 17 is limited. Similarly, base end 122R abuts right arm stop 16.

Figure 4:
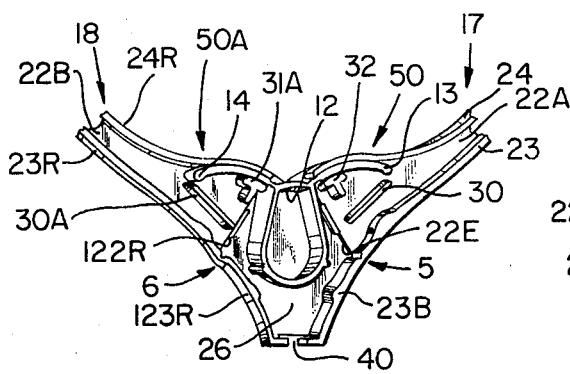
FIG. 4 is a fragmentary perspective view showing the living hinge in minimum spread apart position.
Figure 5:
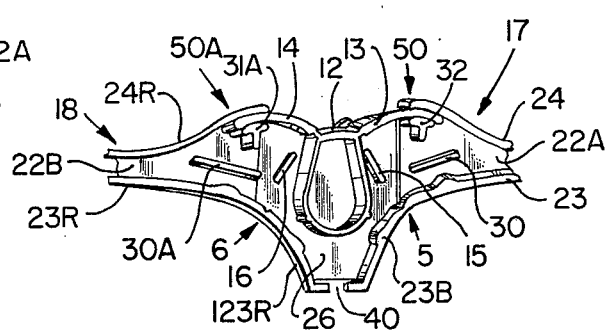
FIG. 5 is a perspective view of FIG. 3.

It is obvious with reference to FIGS. 2 and 3 and/or FIGS. 4 and 5 that left arm 17 and right arm 18 may be adjusted in relative position toward or away from each other in minute increments due to the living hinge.

A pair of sound wave carrying tubes 45, 45A are connected to sound apparatus (not shown) such as the transducer of U.S. Pat. No. 3,463,886 by means of a transducer jack 46 (see FIG. 1). These tubes 45, 45A are ordinarily fabricated from synthetic rubber in order to be flexible. Tube 45 enters channel 22 of left arm 17 and passes through slot 40 and lies between wall 23 and tube guide 30 to be held between walls 23, 24 so as to be attached to ear tip 25. In like manner, tube 45A enters channel 22R of right arm 18 and passes through slot 40 and lies between wall 23R and tube guide 30A to be held between walls 23R, 24R so as to be attached to an ear tip 25.

It is evident that from the point of entry of each tube 45, 45A at slot 40, into and through the respective channel 22, 22R, to the ear tips 25, the tubes are subject to no sharp bends or abrupt turns such as would interrupt the sound wave carrying volume of said tubes.

Having shown and described a preferred embodiment of the present invention by way of example, it should be realized that structural changes could be made and other examples given without departing from either the spirit or scope of this invention.

What we claim is:

1. A stethoscope fabricated as a unitary structure comprising:
a. a body having a left wing and a right wing,
b. a left arm provided with a channel having two walls,
c. friction joint means between one of said two walls and said left wing,
d. the other of said two walls providing hinge attaching means between said left arm and said body,
e. a right arm provided with a channel having two walls, friction joint means between one of said last mentioned two walls and said right wing, the other of said last mentioned two walls providing hinge attaching means between said right arm and said body.

2. In a stethoscope:
a. a body having a left wing and a right wing,
b. a left arm and a right arm,
c. each arm provided with a channel consisting of two walls and a base terminating in a base end,
d. one end of said channel of each arm adapted to receive an ear tip,
e. the opposite ends of said two walls of said left arm terminating, respectfully, in a left wall extension integrally attached to said body, and a section having a cooperating contour with said left wing,
f. said left arm having a friction pad provided with a surface cooperating with said left wing,
g. the opposite ends of said two walls of said right arm terminating, respectfully, in a right wall extention integrally attached to said body, and a section having a cooperating contour with said right wing,
h. said right arm having a friction pad provided with a surface cooperating with said right wing,
i. said left wing slidingly and frictionally engaging said section having a cooperating contour with said left wing and friction pad having a surface cooperating with said left wing,
j. said right wing slidingly and frictionally engaging said section having a cooperating contour with said right wing and friction pad having a surface cooperating with said right wing,
k. said left wall extension pivotally connecting said left arm to said body,
l. said right wall extension pivotally connecting said right arm to said body, and
m. the channel in each arm adapted to receive a sound carrying tube attached to an ear tip on one end.

3. In a stethoscope:
a. a body in the form of a flat plate having a raised elongated collar provided with arcuately shaped oppositely located left wing and right wing,
b. a left arm stop and a right arm stop provided on said body,
c. a left arm and a right arm,
d. each arm provided with a channel consisting of two walls and a base, terminating in a base end,
e. one end of each channel adapted to receive an ear tip,
f. the opposite ends of said two walls of said left arm terminating, respectfully, in a left wing extension integrally attached to said body, and an arcuate section having a cooperating contour with said left wing,
g. said left arm having a friction pad provided with an arcuate surface, and a tube guide,
h. the opposite ends of said two walls of said right arm terminating, respectfully, in a right wall extension integrally attached to said body, and an arcuate section having a cooperating contour with said right wing, i. said right arm having a friction pad provided with an arcuate surface, j. said respective channel, providing stiffening means for said left arm and said right arm, k. said left wing slidingly and frictionally engaging both said arcuate section and said arcuate surface on said left arm to form a left friction joint, l. said right wing slidingly and frictionally engaging both said arcuate section and said arcuate surface, on said right arm, to form a right friction joint, m. said left wall extension pivotally connecting said left arm to said body, n. said right wall extension pivotally connecting said right arm to said body, o. a slot provided between said left wall extension and said right wall extension, and p. a sound tube pathway provided, respectively, between said left wall extension and both said elongated collar and said tube guide on said left arm, and said right wall extension and both said elongated collar and said tube guide on said right arm, and q. the channel in each arm adapted to receive a sound carrying tube attached to an ear tip on one end and guided through said slot and the sound tube pathway and tube guide on the respective arm on the other end.

4. The stethoscope of claim 3 in which the entire structure is fabricated from one piece of plastic.

5. The stethoscope of claim 3 in which the left arm stop and the right arm stop limit the pivotal means of the, respective, left arm and right arm.

* * * * *